United States Patent [19]

Zaiger

[11] Patent Number: Plant 5,461

[45] Date of Patent: May 7, 1985

[54] NECTARINE TREE—ZAIPRIDE CULTIVAR

[75] Inventor: Chris F. Zaiger, Modesto, Calif.

[73] Assignee: Stark Brothers Nurseries and Orchards Company, Louisiana, Mo.

[21] Appl. No.: 525,272

[22] Filed: Aug. 22, 1983

[51] Int. Cl.[3] ..... A01H 5/03
[52] U.S. Cl. ..... Plt./41
[58] Field of Search ..... Plt./41

*Primary Examiner*—Robert E. Bagwill
*Attorney, Agent, or Firm*—Burns, Doane, Swecker & Mathis

[57] ABSTRACT

A new and distinct nectarine variety possessing a relatively low chilling requirement is provided. The fruit of the new variety is early maturing and unlike most low chilling nectarine varieties has a higher level of red skin coloration, and excellent commercial qualities such as firmness and the ability to withstand handling and shipping. The new variety originated as a second generation cross of the Red Grand nectarine variety U.S. Plant Pat. No. 1,060) and the Desert Gold peach variety (non-patented). The new variety of the present invention is particularly suited for growing in the United States in zone 9 and the northern tip of zone 10.

1 Drawing Figure

SUMMARY OF THE INVENTION

The new and distinct variety originated at my experimental orchard at Modesto, Calif. In 1973 seed capable of forming the new variety was planted. This seed was the result of a second generation cross of the Red Grand nectarine variety (U.S. Plant Pat. No. 1,060) and the Desert Gold peach variety (non-patented). More specifically, following the initial controlled cross-pollination, the resulting progeny were allowed to self-pollinate. It was the seed resulting from this self-pollination which was planted.

During 1976 the present variety was selected because of its destinctive characteristics and was initially designated 44G1235. My continued observation of this selection has convinced me that it is a new and distinct variety.

The new variety of the present invention possesses a combination of characteristics which render it particularly suited for the commercial production of quality fruit in many mild southern regions of the United States. The low chilling requirement of the fruit is combined with excellent commercial qualities. More specifically, the new variety may be grown to particular advantage in the United States in zone 9 and in the upper tip of zone 10. The fruit often ripens in early May when grown in such area.

The nectarine tree of the new variety is (a) large, vigorous and upright, (b) possesses a relatively low chilling requirement, and (c) is a productive bearer of good quality, early maturing, medium to large fruit having a high level of red skin coloration and a firm yellow flesh which possesses good eating and shipping qualities.

Asexual propagation at Modesto, Calif. by budding as early as 1976 and subsequent testing by me has demonstrated that the unique combination of characteristics of the new variety comes true to form and is established and transmitted through succeeding propagation. All specimens described herein were grown at Modesto, Calif.

The new nectarine variety has been named the Zaipride cultivar and is being marketed by Stark Brothers Nurseries and Orchards Company under the STARK and GULF PRIDE trademarks.

BRIEF DESCRIPTION OF THE PHOTOGRAPH

The accompanying photograph shows typical specimens of the fruit and foliage of the new nectarine variety in color as nearly true as it is reasonably possible to make the same in a color illustration of this character.

DETAILED DESCRIPTION OF NEW VARIETY

The following is a detailed description of the new variety where color terminology is to be accorded its ordinary dictionary significance except where otherwise indicated. The specimens described were grown at Modesto, Stanislaus County, Calif. 95351.

Representative dates of first and last pickings at Modesto, Calif. are June 15, 1980 and June 20, 1980. It should be understood, however, that when grown in a milder climate such as zone 9 of the United States, the variety of the present inventor will ripen in May.

Tree

Large; vigorous; upright; medium dense; productive; regular bearing.

Trunk:

*Size.*—Medium to stocky.

*Texture.*—Rough to shaggy.

Branches:

*Size.*—Medium.

*Texture.*—Smooth to medium rough.

*Color.*—Brown to light brown.

*Lenticels.*—Large size and medium in number.

Leaves:

*Size.*—Large, approximately $6\frac{1}{2}$ to $7\frac{1}{2}$ inches in length on average and approximately $1\frac{1}{2}$ to 2 inches in width on average.

*Texture.*—Smooth to slightly rough.

*Petiole.*—Approximately $\frac{1}{2}$ inch in length.

*Glands.*—Reinform, 2 to 6 in number, most often approximately 3 in number, located on base of leaf and upper portion of petiole.

*Color-upper surface.*—Dark green, 27-E-8 to 27-F-7 of the Reinhold Color Atlas by A. Kornerup and J. H. Wanscher (1961).

*Color-under surface.*—Dull green, 27-E-5 to 27-E-6 of Reinhold Color Atlas.
*Form.*—Lanceolate, and acutely pointed.
*Margin.*—Crenate.

FLOWERS

Early (at least ten days earlier than Red Grand nectarine variety); representative dates are Feb. 16, 1980 to Feb. 21, 1980 at Modesto, Calif.; bloom period will vary with climatic conditions; blooms are pink in coloration and large and showy.

FRUIT

Maturity when described: Hard ripe — June 15 to 20, 1980.
Size: Medium to large.
*Axial diameter.*—Approximately $2\frac{3}{8}$ to $2\frac{5}{8}$ inches.
*Transverse in suture plane.*—Approximately $2\frac{3}{8}$ to $2\frac{5}{8}$ inches.
Form: Globose; slightly flattened at the stem end.
Suture: Shallow; extends from base to apex.
Ventral surface: Rounded very slightly lipped.
Cavity: Rounded; average depth approximately $\frac{3}{8}$ inch; average breadth approximately $\frac{3}{4}$ inch.
Base: Retuse.
Apex: Rounded to slight depression.
Skin: Medium thickness; medium texture; no tendency to crack; down is wanting.
*Color.*—Bright yellow 4-A-8 to flame yellow 5-A-7 undercolor of the Reinhold Color Atlas, with shading from currant red 9-A-8 to cherry red, 9-B-8 of Reinhold Color Atlas.
Flesh:
*Color.*—Orange yellow 4-A-7 to deep chrome yellow 4-A-8 of Reinhold Color Atlas.
*Texture.*—Firm.
*Juice.*—Moderate.

*Ripens.*—Uniformly.
*Flavor.*—Subacid to mild.
*Fibers.*—Fine and tender.
*Eating quality.*—Good.
Stone: Clingstone.
*Size.*—Medium. Length. — approximately $1\frac{1}{4}$ inch on average. Breadth. — approximately 1 inch on average. Thickness. — approximately $\frac{3}{4}$ inch on average.
*Base.*—Straight to slightly oblique.
*Apex.*—Acuminate.
*Sides.*—Equal to slightly unequal.
*Surface.*—Irregularly furrowed toward apex and pitted toward base.
*Tendency to split.*—Very slight.
*Color.*—Light brown 8-C-4 to 8-D-4 of Reinhold Color Atlas.

USE

Local and long distance market; dessert.

KEEPING QUALITY

Good.

SHIPPING QUALITY

Good.

I claim:

1. A new and distinct variety of nectarine tree, substantially as illustrated and described, characterized by (a) a large, vigorous, and upright growth habit, (b) a relatively low chilling requirement, and (c) the productive formation of good quality, early maturing, medium to large fruit having a high level of red skin coloration and a firm yellow flesh which possesses good eating and shipping qualities.

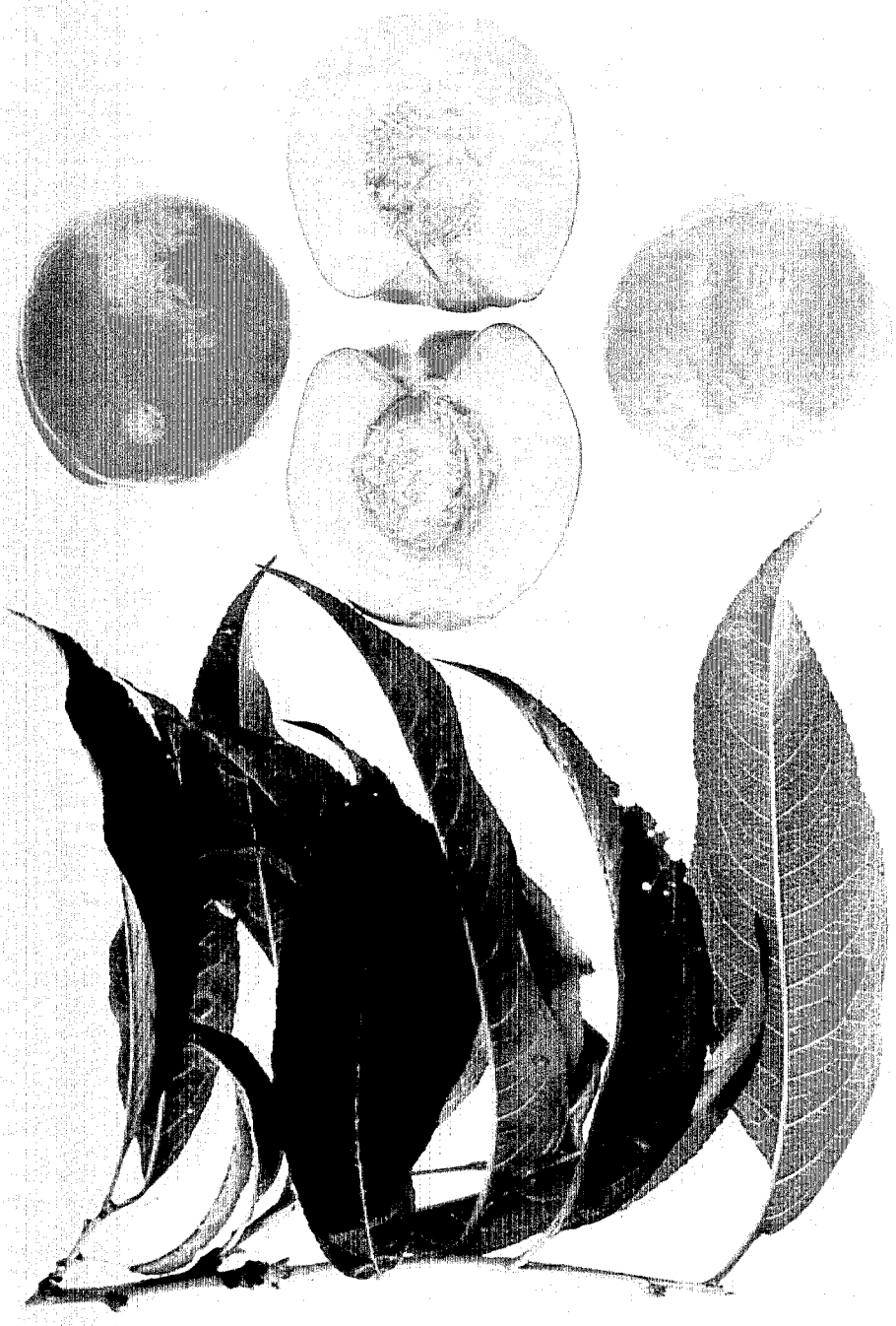

* * * * *